United States Patent [19]

Hutchison et al.

[11] Patent Number: 5,681,606
[45] Date of Patent: Oct. 28, 1997

[54] METHOD OF PREPARING A WATER-BASED BEVERAGE

[75] Inventors: Keith Graeme Hutchison, Quenington; Kelvin Royce Garnett, Cricklade, both of Great Britain

[73] Assignee: R. P. Scherer, Troy, Mich.

[21] Appl. No.: 454,101

[22] PCT Filed: Feb. 11, 1994

[86] PCT No.: PCT/GB94/00280

§ 371 Date: Oct. 10, 1995

§ 102(e) Date: Oct. 10, 1995

[87] PCT Pub. No.: WO94/17788

PCT Pub. Date: Aug. 18, 1994

[30] Foreign Application Priority Data

Feb. 11, 1993 [GB] United Kingdom ............... 9302720

[51] Int. Cl.$^6$ ................... A23C 2/00; A23L 1/05
[52] U.S. Cl. ................... 426/590; 426/89; 426/576; 426/590; 426/592; 426/593; 426/594; 426/597; 426/598; 426/599; 426/648; 426/650; 426/654
[58] Field of Search ................... 426/89, 590, 576, 426/654, 592, 593, 594, 597, 598, 599, 648, 650

[56] References Cited

U.S. PATENT DOCUMENTS 3,620,759  11/1971  Maddox.
4,804,542  2/1989  Fischer et al. ................... 424/456
4,925,683  5/1990  Fischbach et al. ................... 426/590

FOREIGN PATENT DOCUMENTS

| 0 133 636 | 3/1985 | European Pat. Off. . |
| 0 496 705 | 7/1992 | European Pat. Off. . |
| 27 32 527 | 2/1979 | Germany . |
| 30 08 836 | 9/1981 | Germany . |
| 61058537 | 3/1986 | Japan . |
| 87 01034 | 2/1987 | WIPO . |
| 93 25085 | 12/1993 | WIPO . |

*Primary Examiner*—Helen Pratt
*Attorney, Agent, or Firm*—Wallenstein & Wagner, Ltd.

[57] ABSTRACT

A method is disclosed of preparing a beverage in the form of a dilute aqueous solution, suspension or dispersion of an encapsulated product. The capsule is added to a potable liquid, and the capsule material breaks down when submerged in the liquid to release its contents and itself dissolve. A primary advantage of providing the product in this way is that it can be confined within the capsule in liquid form, and can therefore disperse or dissolve in water more readily. Additionally, the capsule would normally sink to the bottom of the body of water before releasing its contents, thereby ensuring that the contents are released within the body of water, and not at the surface thereof.

19 Claims, No Drawings

METHOD OF PREPARING A WATER-BASED BEVERAGE

This application is a 371 of PCT/GB94/00280 filed Feb. 11, 1994 now WO94/17788.

This invention relates to the use of capsules for the storage, packaging and delivery of water soluble or dispersible products. Examples of such products are medicaments, flavourings and functional food products, including vitamin and nutrient supplements.

A number of medicaments are currently available in powder form for dissolving in water to form a palatable and readily ingestible product. Dissolving such medicaments in water also facilitates their subsequent absorption in the body. To enhance the palatability of the drink, the medicament may be combined with flavourings and/or sweeteners, and with an effervescent mixture which results in the drink being carbonated. Medicaments are commonly also provided in tablet and capsule form, ready for swallowing whole. These delivery forms are adapted to breakdown within the body of the patient or user, to release the medicament at an appropriate rate.

The present invention is directed at the provision of a product of the type discussed above for use in dilute aqueous solution, suspension or dispersion, and the preparation of water-based beverages therefrom. The product is confined in a capsule, the material of which is adapted to break down when submerged in water to release the medicament and itself dissolve. A primary advantage of providing the product in this way is that it can be confined within the capsule in liquid form, and can therefore disperse or dissolve in water more readily. Additionally, the capsule would normally sink to the bottom of the body of water before releasing its contents, thereby ensuring that the contents are released within the body of water, and not at the surface thereof.

The ability to confine the capsule contents in liquid form is particularly beneficial for certain flavourings and specifically aromatics. With the contents released within, rather than at the surface of the water, a more stable and long-lasting aroma can be generated. A number of natural products can also be more readily concentrated in stable liquid form than in powder, with minimum need for chemical additives. The avoidance of powder also ensures that the entire dosage within the capsule dissipates in the water. There is no risk of substantial quantities of a medicament for example, remaining in the form of dregs at the base of the glass.

It is known to encapsulate medicinal and food products using capsule material which is itself comestible. The shell material for capsules used in the present invention is normally gelatin based, and as a consequence largely void of flavour, odour and colour.

Suitable capsule materials usually comprise Gelatin and a plasticiser such as Glycerol or sorbitol. A suitable sorbitol is available under the Trade Name ANIDRISORB. The Gelatin forms a matrix for the plasticiser. The relative quantities of these components is important to ensure reliable encapsulation and storage characteristics. However, the dissolution rate of the capsule material can be increased if the amount of Gelatin is reduced, and we have found that the amount of Gelatin can be reduced if a further component is included which forms a secondary matrix for the plasticiser. A typical material includes 18 to 30% by weight of Gelatin and 30 to 45% by weight of Glycerol at the point of encapsulation. In the dried capsule the respective ranges increase to 23 to 38% Gelatin, and 38 to 58% Glycerol. The amount of the further component does not normally exceed 25%, and is usually no more than 12% by weight (15% in the dried capsule). The preferred further component is unbleached starch acetate, most preferably derived from potato, and a suitable product is available under the Trade Name PERFECTAMYL GEL MB from Avebe BA.

The quantities of gelatin specified above are substantially less than is normally used in known gelatin based capsule shell compositions. Similarly, the amount of plasticiser is relatively increased. This is made possible by the presence of the further component which reduces the effect of the plasticiser on the gelatin which might otherwise result in a composition which does not form a structure of strength sufficient for encapsulation and storage. In effect, the further component forms a secondary compatible matrix, typically in the range 20° to 60° C., for the plasticiser within the primary gelatin matrix which does not adversely effect the function of the plasticiser, but reduces its tendency to form an adherent surface on the eventual product. It will be appreciated that a certain quantity of the further component is always required in the composition, and a typical minimum level would be 3% by weight at the point of encapsulation.

Preferred shell materials of the type described above also include a bleached starch acetate, normally derived from potato, and typically in an amount up to 12% by weight. A suitable such potato starch derivative is also available from Avebe BA under the Trade Name PERFECTAMYL GEL 45. This starch derivative is soluble in the manufacture of compositions according to the invention, and therefore remains in solution until the composition dries. At this stage the bleached starch acetate forms a film, thus acting as a bulking agent. It causes a degree of stickiness in the composition as it sets, which is counteracted by the setting of the gelatin and the unbleached starch acetate component. Similar effects can be achieved by using a variety of soluble materials.

The above capsule shell materials and variants thereon are discussed in more detail in British Patent Application No. 9313329.6 in the name of R. P. Scherer Limited, and to which reference is directed. Other suitable materials are described in U.S. Pat. No. 4,804,542 assigned to R. P. Scherer GmbH.

Because, in the practice of the present invention the capsule body will also dissolve in the water, the material of the capsule wall can itself contain significant components contributing to the overall properties of the eventually prepared solution. This is of particular value where the component elements are to be kept separate prior to their use and they may, of course, be kept separate between the capsule material and the encapsulated product. It will be appreciated that the invention may be used in the formation of beverages of the desired strength at any suitable temperature. Drinks may be hot or cold depending upon the treatment being sought.

Various encapsulation techniques can be used in the exploitation of the invention. Two known such techniques are the concentric cylinder and rotary dye methods. The latter has been used for many years by R. P. Scherer Corporation and its associated companies. The process is described in the September 1985 edition of Pharmaceutical Technology, to which reference is also directed.

Products of the kind discussed herein, when provided in liquid form for encapsulation incorporate hydrophobic or hydrophillic carrier media or a combination of both. Examples of hydrophilic solvents or carrier media include: Polyethylene Glycols (PEGs), particularly PEG 400 and PEG 600; Glycofurol; Polyglycerols; propylene Glycol;

Ethanol; Water; Glycerol; transcutol, polysorbate and propylene carbonate.

Hydrophobic solvent/carrier media also include hydrogenated natural oils, synthetic oils such as polymethylsiloxane (dimethicone), neutral oils such as fractionated coconut oil, mineral oils, triacetin, ethyl oleate, and other natural oils such as: Soyabean Oil; Arachis Oil; Corn Oil; Sesame Oil; Olive Oil; Rapeseed Oil; Sunflower Oil and Safflower Oil.

Many products will be formulated with a significant content of oils or other hydrophobic liquids rendering the contents immiscible with aqueous systems and causing an oily surface layer to form when added in water. In order to inhibit the formation of such a surface layer, capsules used in accordance with the invention can include an emulsifier or dispersant, either as part of the contents of the capsule, or in the capsule material itself. Suitable such surfactants are:

- Reaction products of natural or hydrogenated vegetable oils and ethylene glycol; i.e. polyoxyethylene glycolated natural or hydrogenated vegetable oils; e.g. of the type available under the Trade Names CREMOPHOR and NIKKOL;
- Polyeoxyethylene-sorbitan-fatty acid esters; e.g. mono- and tri-lauryl, palmityl, stearyl and oleyl esters; e.g. of the type available under the Trade Name TWEEN;
- Polyoxyethylene fatty acid esters; e.g. polyoxyethylene stearic acid esters of the type available under the Trade Name MYRJ;
- Polyoxyethylene-polyoxypropylene co-polymers; e.g. of the type available under the Trade Names PLURONIC and EMKALYX;
- Polyoxyethylene-polyoxypropylene block co-polymers; e.g. of the type available under the Trade Name POLOXAMER;
- Dioctylsuccinate, dioctylsodiumsulfosuccinate, di-(2-ethylhexyl)-succinate or sodium lauryl sulfate;
- Phospholipids, in particular lecithins; Propylene glycol mono- and di-fatty acid esters such as propylene glycol dicaprylate; propylene glycol dilaurate, propylene glycol hydroxystearate, propylene glycol isostearate, propylene glycol laurate, propylene glycol ricinoleate, and propylene glycol stearate, most preferably propylene glycol caprylic-capric acid diester as is available under the Trade Name MIGLYOL 840;
- Bile salts, e.g. alkali metal salts such as sodium taurocholate;
- Trans-esterification products of natural vegetable oil triglycerides and polyalkylene polyols (e.g. LABRAFIL);
- Mono-, di- and mono/di-glycerides, especially esterification products of caprylic or capric acid with glycerol; e.g. of the type available under the Trade Name IMWITOR;
- Sorbitan fatty acid esters e.g. of the type available under the Trade Name SPAN, including sorbitan-monolauryl, -monopalmityl, -monostearyl, -tristearyl, -monooleyl and trioleyl esters;
- Monoglycerides, e.g. glycerol monooleate, glycerol monopalmitate and glycerol monostearate, for example of the type available under the Trade Names MYVATEX, MYVAPLEX and MYVEROL, and acetylated, e.g. mono- and di-acetylated monoglycerides, for example those available under the Trade Name MYVACET;
- Glycerol triacetate or (1,2,3)-triacetin.

As noted above, capsules used in the practice of the invention can include flavouring and aromatic components, in either the encapsulated contents, or in the capsule shell material itself. Suitable components include essential oils such as lemon, orange and peppermint oils; fruit flavours; aniseed; liquorice; caramel; honey; cream; various spices and combinations of these and other flavours. Such components are supplied by International Flavours & Fragrances, IFF (GB) Ltd. of Haverhill, Suffolk, CB9 8LG ENGLAND. Natural or artificial sweeteners can also be used, such as:

Aspartame, Saccharin, Acesulphame K, Neohesperidine hydrochloride, Mannitol, Xylitol, and Maltitol;

taste-masking ingredients such as sodium bicarbonate, ion exchange resins, cyclodextrins and adsorbates;

suspending agents such as beeswax, hydrogenated vegetable oils, glycerol monostearate or glycerol palmitate, and high molecular weight PEGs; e.g. 1500 to 6000.

Where the encapsulated contents include particles in suspension, the particles may be separately coated, typically with suitably sweetened or flavoured coatings, such as those referred to above. Such a coating can serve as either or both of a taste-masking agent and a stabiliser in the suspension.

By way of further illustration of the invention some contents formulations, and capsule wall compositions will be given by way of example, with the results of some tests thereon.

I Contents Formulations

EXAMPLE 1

| Fractionated Coconut Oil BP/PhEur | 75% |
|---|---|
| Gelucire 42/12* | 7% |
| Span 20** | 3% |
| Mannitol BP | 9% |
| Aspartame US NF XVII | 1% |
| Flavour | 5% |
| | 100% |

*Glycerides and polyglycerides of fatty acids of vegetable origin.
**Sorbitan fatty acid esters (BP 1980)

EXAMPLE 2

| Imwitor 742* | 80% |
|---|---|
| Tween 80** | 14% |
| Aspartame US NF XVII | 1% |
| Flavour | 5% |
| | 100% |

*Caprylic/Capric mono-di & tri-glycerides (Medium chain partial glycerides US NF XVII)
**Polysorbate 80 BP

EXAMPLE 3

| Polyethylene Glycol 400 BP | 56% |
|---|---|
| Glycerol BP | 8% |
| Water, Purified BP | 5% |
| Mannitol BP | 25% |
| Aspartame US NF XVII | 1% |
| Flavour | 5% |
| | 100% |

EXAMPLE 4

| Lycasin 80/55* | 88.5% |
|---|---|
| Aerosil 200** | 1.5% |
| Glycerol BP | 5% |
| Flavour | 5% |
| | 100% |

*Hydrogenated Glucose Syrup
**Colloidal Silicon Dioxide

EXAMPLE 5

| Fractionated Coconut Oil BP | 58% |
|---|---|
| Tween 80* | 25% |
| Mannitol BP | 10% |
| Sodium Saccharin BP | 2% |
| Flavour | 5% |
| | 100% |

*Polysorbate 80 BP

EXAMPLE 6

| Fractionated Coconut Oil BP | 95% |
|---|---|
| Flavour | 5% |
| | 100% |

EXAMPLE 7

| Fractionated Coconut Oil BP/Ph Eur | 75% |
|---|---|
| Gelucire 42/12 | 7% |
| Span 20 | 3% |
| Mannitol BP | 9% |
| Peppermint Oil BP | 6% |
| | 100% |

EXAMPLE 8

| Fractionated Coconut Oil BP/Ph Eur | 75% |
|---|---|
| Gelucire 42/12 | 7% |
| Span 20 | 3% |
| Mannitol BP | 9% |
| Aspartame US NF XVII | 1% |
| Peppermint Oil BP | 5% |
| | 100% |

EXAMPLE 9

| Polyethylene Glycol 400 BP | 53.3% |
|---|---|
| Glycerol BP | 7.6% |
| Water Purified BP | 4.8% |
| Paracetamol BP | 28.6% |
| Aspartame US NF XVII | 1.0% |
| Lemon Flavour 17.42.7201 | 4.8% |
| | 100% |

EXAMPLE 10

| Polyethylene Glycol 400 BP | 53.3% |
|---|---|
| Glycerol BP | 7.6% |
| Water Purified BP | 4.8% |
| Paracetamol BP | 28.6% |
| Saccharin, Sodium BP | 1.0% |
| Lemon Flavour 17.42.7201 | 4.8% |
| | 100% |

II Gelatin Melts for Capsule Wall

EXAMPLE A

| Gelatin 150 Bloom | 43.36% |
|---|---|
| Glycerine BP | 20.01% |
| Purified Water BP/EP | 36.63% |

EXAMPLE B

| Gelatin 150 Bloom | 38.41% |
|---|---|
| Glycerine BP | 29.18% |
| Purified Water BP/EP | 32.41% |

EXAMPLE C

| Gelatin 195 Bloom | 26.00% |
|---|---|
| Glycerine BP | 36.00% |
| Purified Water BP/EP | 22.00% |
| Perfectamyl Gel MB | 6.00% |
| Perfectamyl Gel 45 | 10.00% |

EXAMPLE D

| Gelatin 160 Bloom | 43.20% |
|---|---|
| Anidrisorb 85/70 | 24.80% |
| Purified Water BP/EP | 32.00% |

EXAMPLE E

| Gelatin 195 Bloom | 25.00% |
|---|---|
| Glycerine BP | 24.00% |
| Purified Water BP/EP | 23.00% |
| Sorbitol Syrup 70% BP | 12.00% |
| Perfectamyl Gel MB | 6.00% |
| Perfectamyl Gel 45 | 10.00% |

Examples A, B and D were prepared by standard techniques and sampled into 1 kg bottles. Example B was prepared by adding 65.0 g of glycerine BP to 500 g of the gel melt of Example A. Examples C and E were prepared in the laboratory micrometer on a 1 kg scale using the following method:

Add water and glycerine (or Anidrisorb) together and put into the vessel. Add the gelatin powder with stirring and allow to 'crumb' under vacuum for 10 minutes. Using a waterbath with circulator, heat the vessel to 90° C. and allow to stand at temperature for 35 minutes. Deaerate the gel mass using a vacuum pump and trying to avoid water loss. (If starches are being used in the gel mass, add to the water and plasticiser before adding the gelatin powder.)

Colouring and flavouring was then added to some of the prepared melts as follows:

EXAMPLE F

To 250 g of gel mass of Example D add:

| Quinoline Yellow | 0.01 g |
|---|---|
| Carmine Red | 0.13 g |

EXAMPLE G

To 250 g of gel mass of Example C add:

| Curcumin | 0.20 g |
|---|---|
| Yellow Iron Oxide Paste | 0.38 g |
| Titanium Dioxide Susp. | 6.00 g |
| Citric Acid BP | 1.25 g |
| Aspartame US NF XVII | 1.00 g |
| Lemon Oil | 5.00 g |

EXAMPLE H

To 200 g of gel mass of Example E add:

| Quinoline Yellow | 0.40 g |
|---|---|
| Titanium Dioxide Susp. | 2.00 g |

EXAMPLE I

To 200 g of gel mass of Example E add:

| Titanium Dioxide Susp. | 4.00 g |
|---|---|

90 mm ribbons of each of the coloured gels and natural gel masses were cast. 1.8 cm circles were cut into each of the ribbons which were then dried.

Capsules were manufactured with shells prepared from the melts of Example I and H, and filled respectively with the contents formulations of Examples 7 and 9.

Each contents formulations was checked for dispersion properties at 70° C. in both stirred and unstirred water.

2 ml portions of each mix were measured into syringes. These portions were each injected into beakers containing 250 ml of water at 70° C. and cooling naturally. The appearance of the resulting mixture was then noted. This test was then repeated with a gentle paddle stirring action.

The density of Examples 7 to 10 was then determined and capsules with equivalent fill density were dropped into 250 ml of water at 70° C. to see if they sank to the bottom before rupturing.

Each prepared gel disc was tested for disintegration in water at various temperatures.

| 30° C. | } Tested in BP disintegration apparatus without using Perspex discs |
|---|---|
| 37° C. | |
| 50° C. | |
| 70° C. cooling naturally | } Tested on a hotplate stirrer with paddle stirring. |
| Boiling | |

| Boiling water cooling naturally | } Temperature checked using a thermometer. |
|---|---|

Disintegration time was noted for each of the gel types at each temperature to the nearest 5 seconds.

Discs prepared from the melts of Examples F and G were also tested for disintegration at 37° C., 70° C. and the time for rupture and full disintegration noted.

The capsules were tested for disintegration and fill dissolution at various temperatures and using different methods for adding the capsules to the water.

| 70° C. Cooling naturally | Addition of capsule to 70° C. water which is stirred from the bottom |
|---|---|
| Boiling Cooling naturally | Addition of capsule to boiling water which is stirred from the bottom |
| Boiling Cooling naturally | Addition of boiling water to a capsule in a 'mug' and stirring with a teaspoon |

Disintegration times were noted for each of the capsules, to the nearest 5 seconds.

Contents Formulations Dispersion Properties

| Example | Unstirred water 70° C. | Stirred water 70° C. | "Sediment" Formation |
|---|---|---|---|
| 1 | Instant dispersion No oily layer | Instant dispersion No oily layer | None |
| 2 | Poor dispersion Oily layer | Poor dispersion Oily layer | None |
| 3 | Good dispersion No oily layer | Good dispersion No oily layer | None |
| 4 | Good dispersion No oily layer | Good dispersion No oily layer | None |
| 5 | Good dispersion Slight oily layer | Good dispersion Slight oily layer | None |
| 6 Control | No dispersion Oily layer | No dispersion Oily layer | None |
| 7 | Good dispersion Slight oily layer | Good dispersion Slight oily layer | None |
| 8 | Good dispersion Slight oily layer | Good dispersion Slight oily layer | None |
| 9 | Good dispersion No oily layer | Good dispersion No oily layer | None |
| 10 | Good dispersion No oily layer | Good dispersion No oily layer | None |

No dispersion Oil floats on surface
Instant dispersion No oil floats on surface
Good dispersion Takes 5 sec or less to disperse. No oil floats on surface.
Poor dispersion Takes >5 sec to disperse. Some oil floats on surface.

Gel Discs Disintegration

| Example | 30° C. | 37° C. | 50° C. | 70° C./ cooling | Boiling | Boiling/ cooling |
|---|---|---|---|---|---|---|
| A | 12:20 | 03:05 | 02:20 | 02:25 | 00:35 | 01:30 |
| B | 11:40 | 04:10 | 02:10 | 01:45 | 00:20 | 00.40 |
| C | 17:00 | 04:10 | 01:30 | 01:30 | 00:30 | 00:40 |
| D | 14:30 | 05:40 | 03:05 | 02:45 | 02:10 | 01:45 |
| E | 22:00 | 03:50 | 01:30 | 01:00 | 00.25 | 00:40 |

-continued

Gel Discs Disintegration

| Example | 30° C. | 37° C. | 50° C. | 70° C./ cooling | Boiling | Boiling/ cooling |
|---|---|---|---|---|---|---|
| F | Not tested | 09:55 | Not tested | 05:00 | Not tested | Not tested |
| G | Not tested | 06:00 | Not tested | 02:00 | Not tested | Not tested |
| H | 18:00 | 03:45 | 01:30 | 01:30 | 00:15 | 00:25 |
| I | 17:00 | 03:25 | 01:50 | 02:20 | 00:15 | 00:35 |

All times are shown in minutes:seconds

Capsule Performance

| | Capsule added to boiling water with stirring | Boiling water added to capsule with stirring | 70° C./cooling naturally |
|---|---|---|---|
| 9 + H -fill | 00:28 | 00:17 | 00:23 |
| 9 + H -shell | 01:06 | 00:43 | 02:15 |
| 7 + I -fill | 00:20 | Immediate | 00:05 |
| 7 + I -shell | 00:45 | 00:38 | 01:50 |

All times are shown in minutes:seconds
Shell rupture immediate in all cases.

SUMMARY

Contents Formulations

From the Results it can be seen that Example 1 exhibited the best and quickest dispersion of all the mixes in both stirred and unstirred water. Examples 3 and 4 also displayed good dispersion properties, although the dispersion was slow due to the thicker nature of the mixes than in Example 1. Example 5 showed good dispersion properties although a slight surface layer of oil could be detected even after stirring.

All of the Examples, including the Control, had good flavour/odour release and had no sediment formation on standing.

Gel Discs

From the Data table it can be seen that the discs from the melts of Examples C and E do show a decrease in disintegration time relative to the standard melts of Examples A, B and D, but this is mainly noticed at elevated temperatures and the advantage is minimal at lower temperatures. When the gels are coloured and flavoured, the disintegration time is again reduced, when compared to the uncoloured and unflavoured gel masses.

Capsules

Both capsules tested exhibit excellent disintegration characteristics in boiling water, the best of which are shown using the method of adding boiling water to the capsule and stirring. At 70° C. the rate of capsule disintegration slows but a good solution of gelatin and fill material can still be made in approximately 2 minutes.

The slightly slower dissolving time for the lemon flavoured (Example 9) capsule is believed to be due to the fill removing plasticiser from the shell and causing it to harden.

It will be readily appreciated that a wide range of products may be used in encapsulated form according to the invention. A list of therapeutic categories and active ingredients, which is by no means exhaustive, is set out below. It should be understood that two or more of the agents may be incorporated in the same capsule.

| | | | |
|---|---|---|---|
| 1. | Decongestant | (a) | Phenylpropanolamine hydrochloride |
| | | (b) | Pseudoephedrine hydrochloride |
| | | (c) | Aromatic oils for inhalant e.g., Eucalyptus Oil, Menthol, and Camphor |
| 2. | Anti-Tussives | (a) | Dextromethorphan (hydrobromide or salt or free base) |
| | | (b) | Codeine phosphate |
| 3. | Expectorant | (a) | Ammonium chloride |
| | | (b) | Guaiphenesin |
| 4. | Analgesic | (a) | Paracetamol |
| | | (b) | Ibuprofen |
| | | (c) | Naproxen |
| | | (d) | Naproxen Sodium |
| 5. | Antacid | (a) | Aluminum hydroxide gel |
| | | (b) | Magaldrate |
| | | (c) | Magnesium trisilicate |
| 6. | Gastritis | (a) | Ranitidine |
| | | (b) | Cimetidine |
| 7. | Anti-flatulent | (a) | Simethicone |
| | | (b) | Dimethicone |
| 8. | Gastric Reflux Suppressant | (a) | Alginic Acid |
| 9. | Laxative | (a) | Docusate sodium |
| | | (b) | Sodium picosulphate |
| | | (c) | Isphagula husk |
| 10. | Anti-spasmodic | (a) | Hyoscine butylbromide |
| | | (b) | Peppermint oil |
| | | (c) | Mebeverine hydrochloride |
| | | (d) | Metaclopramide hydrochloride |
| 11. | Cystitis | (a) | Potassium citrate |
| 12. | Anti-fungal (topical) | (a) | Miconazole nitrate |
| | | (b) | Tolnaftate |
| 13. | Anti-bacterial (topical) | (a) | Chlorhexidine gluconate |
| | | (b) | Triclosan |
| 14. | Scabies (topical) - anti mite/ anti-lice | (a) | Lindane |
| | | (b) | Phenothrin |
| 15. | Antihistamine | (a) | Diphenylhydramine hydrochloride |
| | | (b) | Bromopheniramine Maleate |
| | | (c) | Doxylamine Succinate |

While the above list itemizes essentially medicinal compounds, it should be understood that the invention is also suitable for the use of encapsulated functional foods for use in products such as concentrated liquid foods and drinks. Other applications include flavourings for foods with additional vitamins or nutrient content; spices and health food products such as garlic.

We claim:

1. A method of preparing a water-based beverage wherein a capsule in the form of a shell enclosing an additive is added to a potable aqueous liquid, the shell breaking down to release the additive into the liquid, and itself dissolving in the liquid, wherein the shell is water-soluble and comprises gelatin and a plasticizer, the gelatin providing a primary matrix for the plasticizer, and a further component providing a secondary matrix for the plasticizer, wherein the material of the capsule shell comprises by weight 23% to 38% gelatin and 38% to 58% plasticizer.

2. A method according to claim 1 wherein the material of the capsule shell comprises by weight no more than 15% of the further component.

3. A method according to claim 1, wherein the additive is water-soluble.

4. A method according to claim 1, wherein the potable liquid comprises water heated to 70° C.

5. A method according to claim 1, wherein the shell of the capsule ruptures to release its contents prior to its dissolution.

6. A method according to claim 1, wherein the capsule is adapted to sink to a lower portion of the liquid prior to releasing the additive.

7. A method according to claim 1, wherein the additive is in liquid form.

8. A method according to claim 1, wherein the secondary matrix is an acetate.

9. A method according to claim 1, wherein the additive comprises at least one of a flavoring and a fragrance generator.

10. A method according to claim 1, including an ingredient included in the capsule, the ingredient comprising at least one of an emulsifier and a dispersant.

11. A method according to claim 10, wherein the ingredient is included with the additive.

12. A method according to claim 10, wherein the ingredient is included in the material of the shell.

13. A method of preparing a water-based beverage comprising adding to a potable aqueous liquid a sealed capsule enclosing an additive in which the capsule shell comprises by weight 38% to 58% of a plasticizer selected from glycerol and sorbitol, 23% to 38% gelatin, and up to 15% unbleached starch acetate, the gelatin and acetate providing primary and secondary matrices for the plasticizer, the shell dissolving in the aqueous liquid and releasing the additive.

14. A method, according to claim 13, wherein the potable liquid comprises water heated to 70° C.

15. A method according to claim 13, wherein the capsule is adapted to sink to a lower portion of the liquid prior to releasing the additive.

16. A method according to claim 13, wherein the additive is in liquid form.

17. A method according to claim 13, wherein the additive comprises a medicament.

18. A method according to claim 13, wherein the additive comprises at least one of a flavoring and a fragrance generator.

19. A method according to claim 13, including an ingredient included in the capsule, the ingredient comprising at least one of an emulsifier and a dispersant.

* * * * *

UNITED STATES PATENT AND TRADEMARK OFFICE
CERTIFICATE OF CORRECTION

PATENT NO. : 5,681,606
DATED : October 28, 1997
INVENTOR(S) : KEITH GRAEME HUTCHISON and KELVIN ROYCE GARNETT It is certified that error appears in the above-identified patent and that said Letters Patent is hereby corrected as shown below:

Column 6, Line 59, "micrometer" should be -- micromelter--.

Signed and Sealed this

Seventh Day of April, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,681,606
DATED : Oct. 28, 1997
INVENTOR(S) : Keith Graeme Hutchison, et al It is certified that error appears in the above-identified patent and that said Letters Patent is hereby corrected as shown below:

On title page, item [73] Assignee, should read --R. P. Scherer Corporation, Troy, Mich.--

Signed and Sealed this

Nineteenth Day of October, 1999

Attest:

Q. TODD DICKINSON

*Attesting Officer*  *Acting Commissioner of Patents and Trademarks*